United States Patent [19]

Ellison et al.

[11] Patent Number: Plant 6,966

[45] Date of Patent: Aug. 1, 1989

[54] ASPARAGUS PLANT—'TARA'

[75] Inventors: J. Howard Ellison, Milltown; John J. Kinelski, Princeton, both of N.J.

[73] Assignee: Rutgers University, New Brunswick, N.J.

[21] Appl. No.: 159,681

[22] Filed: Feb. 24, 1988

[51] Int. Cl.[4] ..... A01H 5/00

[52] U.S. Cl. ..... Plt./89

[58] Field of Search ..... Plt./89

*Primary Examiner*—James R. Feyrer

*Attorney, Agent, or Firm*—Frank B. Robb

[57] ABSTRACT

A female Asparagus plant which when combined sexually with a male plant produces an F 1 all male hybrid and transmits rust and Fusarium resistance to its progeny when asexually propagated.

1 Drawing Sheet

1

This invention relates to a new and distinct variety of Asparagus which is a female plant and we have chosen to emphasize that fact by denominating the same with the female name "Tara" where commercial designation is necessary.

In view of our long continuing program of breeding for improvement of Asparagus plants to establish various factors such as resistance to rust (*Puccinia asparagi*) and tolerance to Fusarium infestation, the development of the instant plant is important since we have found that those characteristics are transmitted to successive generations.

We have determined this by effecting asexual reproduction for the purposes of establishing that the characteristics come true in successive generations, by both crown division and tissue culture.

Further in our program, we are constantly on the lookout for Asparagus plants in many different areas, which have resistance to rust, tolerance to Fusarium infestation, are vigorous, high headed, produce jumbo size spears, and result in large volume production among other desirable characteristics, all looking to increase commercial production and value.

Thus when this new Asparagus plant was found to have resistance to rust, tolerance to Fusarium infestation, and also be a female plant, it was used to combine sexually with the male "Scott Howard", U.S. Plant Pat. No. 5,549 and thus the F1 all male hybrid "Jersey Titan" was produced. This hybrid "Jersey Titan" is the subject of separate application.

The fact that our new variety was selected from the cross 14×30, cross No. 277, and because of "Tara's" rust and Fusarium tolerance and the further fact that those characteristics are in fact transmitted by asexual propagation, support our selection and enhance the value of the long continuing program which we have undertaken.

2

DETAILED BOTANICAL DESCRIPTION

Figure 2:
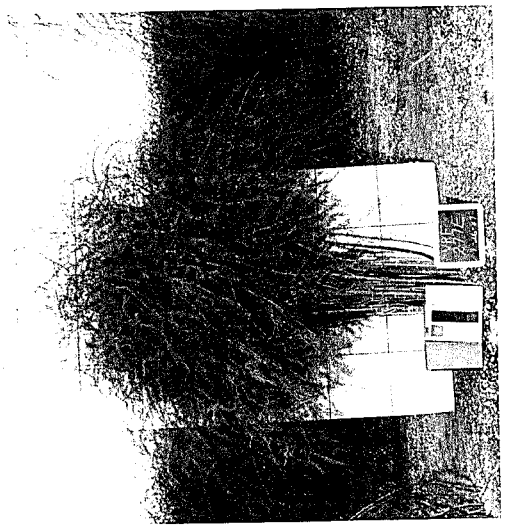
FIG. 2 is a color photograph of a typical specimen of 'Tara' in an observation planting showing the speciment inside view, in color and as nearly representative of such a plant as is possible to disclose the same in a reproduction of this kind, color references being those related to the Munsell Limit Color Cascade of Macbeth Division of Kollmorgen Corporation.
Figure 1:
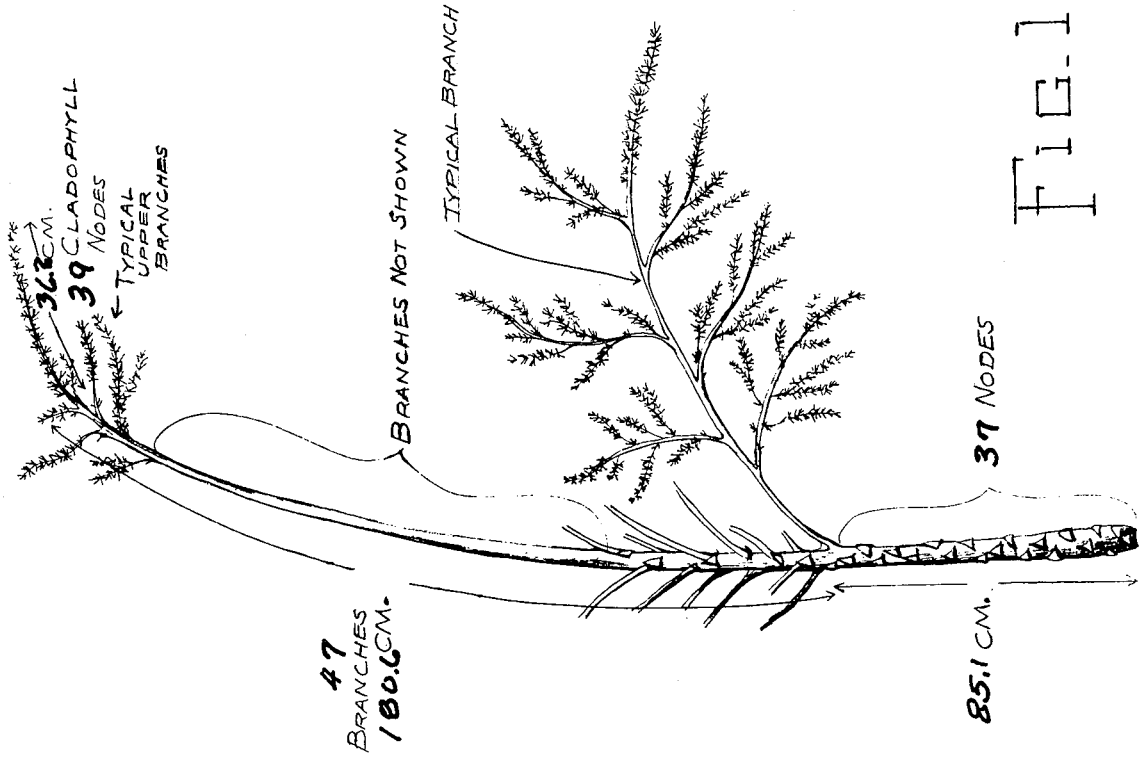
FIG. 1 is a mechanical drawing showing portions of a mature Asparagus plant showing characteristic dimensions of a typical specimen of 'Tara'.

As part of that program and records kept in relation thereto, we have assembled data set forth herinafter which assists us in distinguishing among the many plants produceed, the data being representative of such a plant and in this case a specific plant "Tara".

ASPARAGUS PLANT DATA

| ASPARAGUS PLANT NO. TARA (277E) | Inch × 2.54 = cm. |
|---|---|
| STALK DATA | |
| The values to follow are expressed in centimeters unless otherwise indicated. The number "1" in parenthesis below, indicates that the measurements presented were taken from the largest stalk. | |
| Number of nodes below first branch(1) | 37 |
| Number of cm. from crown to first branch(1) | 85.1 |
| Number of branches(1) | 47 |
| Number cm. between first and last branch(1) | 180.0 |
| Internode length in cm. between branches | 3.83 |
| Number of cladophyll nodes beyond last branch(1) | 39 |
| Number of cm. beyond last branch(1) | 36.2 |
| Internode length in cm. beyond last branch(1) | 0.93 |
| Largest stalk diameter in mm | 23.0 |
| Mean diameter of three largest stalks in mm | 22.0 |
| Number of stalks | 35 |
| Stalk vigor index(Number × mean diameter) | 16,940 |
| Mature stalk color, bloom removed | 21-12 |
| Crown to first branch of highest headed stalk cm | 85.1 |
| Length of highest headed stalk cm | 301.0 |
| FLOWER DATA | |
| Petal tip (yellow) | 25.3-3.1 |
| Petal base (green) | 21.8-9.6 |
| Flower length mm | 4.96 |
| Flower width at midpoint mm | 2.38 |
| FRUIT DATA (277E × 22-8) | |
| Weight of 100 fruit (g) | 26.8 |
| Water displacement of 100 fruit (ml) | 30.0 |
| Number of seed per 100 fruit | 216 |
| Weight of seed per 100 fruit | 7.0 |
| Mean weight per seed (g) | 0.0324 |
| Water displacement of seed of 100 fruit (ml) | 8.0 |
| Mature fruit color | 32-12 |
| CLADOPHYLL DATA | |
| Number per node | 4.60 |
| Length (mm) | 19.4 |
| Width (mm) | 0.136 |

We claim:

1. A new and distinct variety of Asparagus plant substantially as herein shown and described, characterized particularly as to novelty by its ability to transmit rust (*Puccinia asparagi*) and Fusarium tolerance, when asexually propagated as well as produce an all male hybrid when combined sexually with a male hybrid.

* * * * *